US00PP26160P3

(12) United States Plant Patent
Korlipara

(10) Patent No.: US PP26,160 P3
(45) Date of Patent: Nov. 24, 2015

(54) ***ECHINACEA* PLANT NAMED 'DIXIE SUN'**

(50) Latin Name: ***Echinacea* spp.**
Varietal Denomination: Dixie Sun

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 184 days.

(21) Appl. No.: 13/998,594

(22) Filed: Nov. 14, 2013

(65) Prior Publication Data

US 2015/0135385 P1 May 14, 2015

(51) Int. Cl.
*A01H 5/02* (2006.01)

(52) U.S. Cl.
USPC ..... Plt./428

(58) Field of Classification Search
USPC ..... Plt./428
See application file for complete search history.

(56) References Cited

PUBLICATIONS

Terra Nova Nurseries—Mobile—Introduction—E, retrieved on Jul. 7, 2015, retrieved from the Internet at <http://www.terranovanurseries.com/mobile/pages/introductions_e.html> 3 pp.*

* cited by examiner

*Primary Examiner* — June Hwu
(74) *Attorney, Agent, or Firm* — Klarquist Sparkman, LLP

(57) ABSTRACT

A new and distinct *Echinacea* plant named 'Dixie Sun' characterized by an amazing number of inflorescences starting in the first season, very long bloom time with excellent rebloom, a very upright, compact habit, bright orange yellow young ray florets that mature to yellow, numerous, strong stems, and excellent vigor.

1 Drawing Sheet

Botanical denomination: *Echinacea* spp.
Variety designation: 'Dixie Sun'.

BACKGROUND OF THE INVENTION

The present invention relates to a new and distinct cultivar of *Echinacea* and given the cultivar name 'Dixie Sun'. *Echinacea* is in the family Asteraceae. The new cultivar is part of a planned breeding program for a landscape series with compact habits and profuse inflorescences. The exact parents of this selection are unknown, unnamed, proprietary interspecific hybrids bred from *Echinacea paradoxa, Echinacea purpurea*, and *Echinacea tennesseensis.*

Compared to *Echinacea* 'Sunbird' (U.S. Plant Pat. No. 22,631), the new cultivar has ray florets that are more yellow, a flatter inflorescence, and a shorter narrower habit.

Compared to *Echinacea* 'Cleopatra', US Plant Patent applied for, the new cultivar has darker yellow ray florets that mature to medium yellow rather than yellow ray florets that lighten to cream.

This new *Echinacea* cultivar is uniquely distinguished by:

1. an amazing number of inflorescences starting in the first season,
2. very long bloom time with excellent rebloom,
3. very upright, compact habit,
4. bright orange yellow young ray florets that mature to yellow,
5. numerous, strong stems, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows the inflorescences and habit of *Echinacea* 'Dixie Sun' as a one-year-old growing in the trial field in full sun in early September in Canby, Oreg.

DETAILED PLANT DESCRIPTION

The following is a detailed description of the new *Echinacea* cultivar based on observations of nine-month-old specimens growing in the garden in July in part sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, $5^{th}$ edition.

Plant:

*Type*.—Herbaceous perennial.
*Hardiness*.—USDA Zones 4 to 9.
*Size*.—Grows to about 23 cm wide and 53 cm tall to top of inflorescences.
*Form*.—Basal clump, with 1 to 8 stems from the base.
*Vigor*.—Excellent.

*Roots*.—Fibrous, with many downward growing and few laterals, ivory in color, Yellow White 158D, roots develop easily from cuttings from the crown.

Leaf (stem):

*Type*.—Simple.

*Shape*.—Lanceolate.

*Arrangement*.—Alternate.

*Blade size*.—Grows to 9 cm long and 3 cm wide.

*Margins*.—Entire.

*Apex*.—Acuminate.

*Base*.—Attenuate.

*Surface texture*.—Strigose on both sides.

*Venation*.—Pinnate, Yellow Green 148D on both sides.

*Color*.—Topside Yellow Green 147A, bottom side closest to Yellow Green 147B.

*Petiole description*.—Clasping, grows to 3 cm long and 4 mm wide, scabrous, narrow leafy edges which fold upwards, topside Yellow Green 147A, bottom side Yellow Green 148D.

Inflorescence:

*Type*.—Composite on terminal stalked heads.

*Number of flowering stems from the ground*.—1 to 3.

*Flowering stem*.—Grows to 50 cm tall from the base of the plant to the terminal inflorescence and can grow to 16 cm long from the top stem leaf to the base of an inflorescence; unbranched to branched, with 1 to 3 inflorescences per stem; diameter growing to 7 mm wide near the inflorescence; strigose; Yellow Green 147B.

*Size*.—Grows to 9.5 cm wide and 5.5 cm deep as disc enlarges.

*Form*.—Ray florets held horizontally, mature disc is conic.

*Immature inflorescence* (*bud*).—4 cm wide and 3 cm deep, ray florets held upright at an 60 degrees and rolled up so only the back color shows, Yellow 14D, disc color Yellow Green 144A.

*Ray florets*.—Without pistil or stamen, about 20 in number, grow to 45 mm long and 14 mm wide, oblanceolate with the tip two-to-three-toothed (each acute), entire margins, base attenuate, glabrous on both sides; topside new florets Yellow Orange 17A, old florets maturing to Yellow Orange 16B; bottom side Yellow Orange 19C on young florets to Green Yellow 1C on old florets.

*Disc*.—Flat becoming conic, becoming 30 mm deep and 35 mm wide with maturity, Yellow Green 144A in background with bracts Orange 21A.

*Disc florets*.—About 300 in number, each with 1 pistil and 4 stamen, grow to 10 mm long and 2.5 mm wide, each with one persistent, very stiff linear bract (12 mm long with the top 3 mm between Orange 20A and Green 138A blending to 2 mm Green 138A blending to White NN155A on bottom); corolla 6 mm long and 2 mm wide, tubular, 5 lobed, glabrous, Green 138A on lobes to 149D in middle and 138B on base; pistil 9.5 mm long, ovary 3 mm long, White NN155D with top Yellow Green 144A, style 5.5 mm long White NN155A, 2-branched stigma spreading 2.5 mm wide, Green 138B; stamen 5 mm long, filaments 2 mm long and White NN155B, anthers 3 mm long and Black 202A, pollen Yellow Orange 21A.

*Involucral bracts*.—In 4 leafy series, area grows to 30 mm wide and 8 mm deep, lobes lanceolate in shape, reflexed, grow to 5 mm long and 4 mm wide, Green N137A, margins strigose, tip acute, strigose on both sides.

*Receptacle*.—Grows to 6 mm wide and 14 mm deep, White NN155B.

*Bloom period*.—July through October in Canby, Oreg.

*Fragrance*.—Floral, sweet.

*Lastingness*.—Each inflorescence lasts about two weeks in Canby, Oreg.

Seeds: 3 mm long and 2.5 mm wide, oval, Brown 200C.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

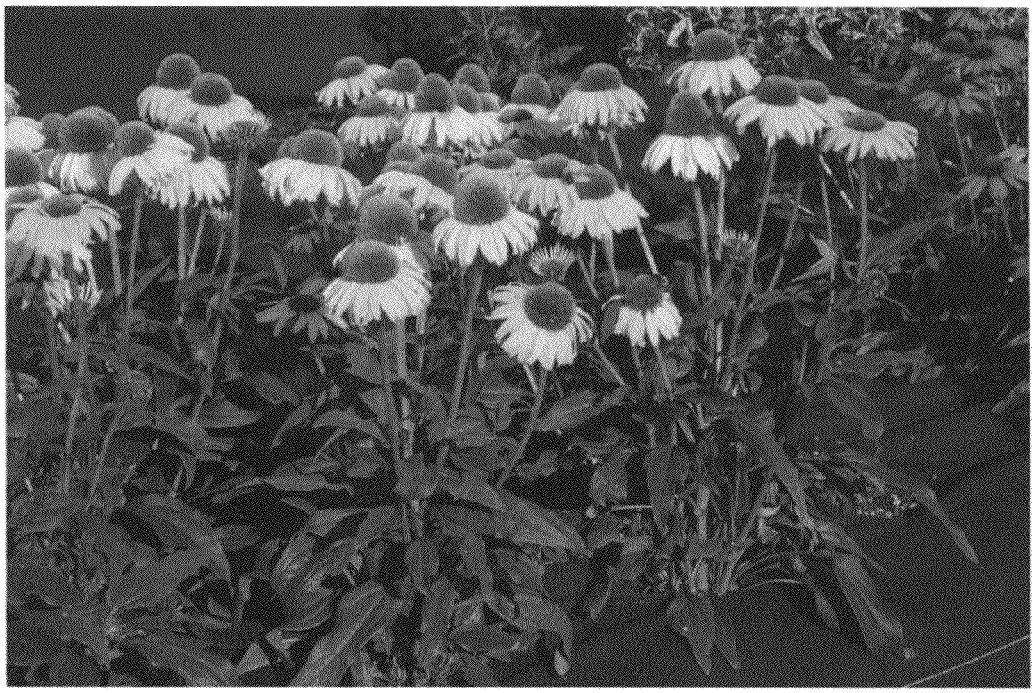

* * * * *